Figure 1:
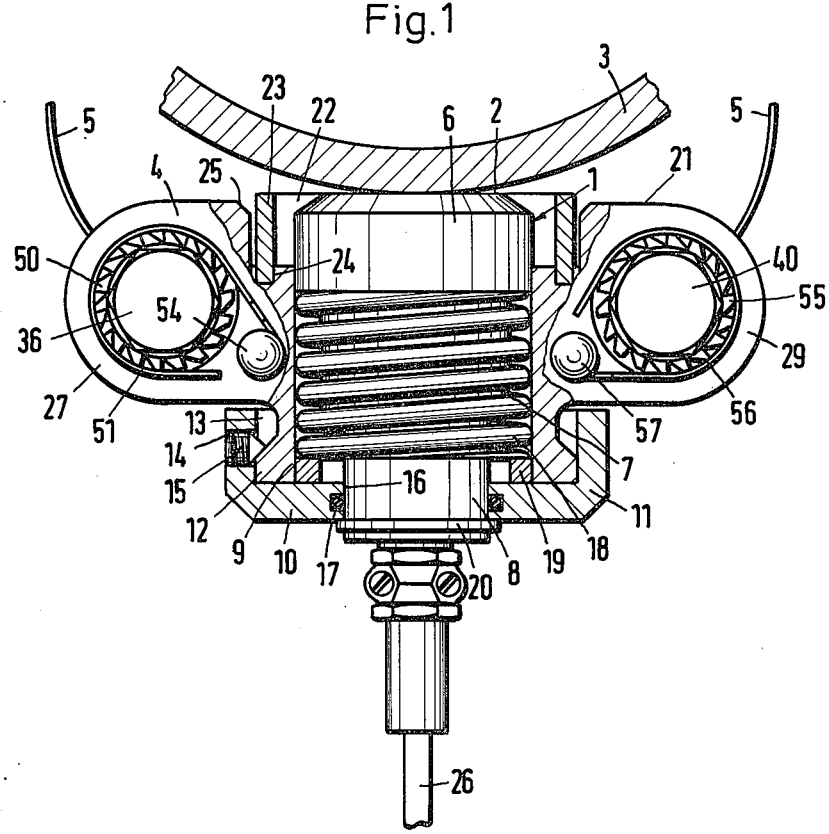

United States Patent [19]

Rottmar

[11] 4,242,744
[45] Dec. 30, 1980

[54] FIXING OF SONIC TRANSDUCER TO A CONTAINER

[75] Inventor: Werner Rottmar, Loerrach, Fed. Rep. of Germany

[73] Assignee: Endress u. Hauser GmbH u. Co., Maulburg, Fed. Rep. of Germany

[21] Appl. No.: 944,558

[22] Filed: Sep. 21, 1978

[30] Foreign Application Priority Data

Sep. 27, 1977 [DE] Fed. Rep. of Germany ....... 2743394

[51] Int. Cl.³ .............................................. G01H 1/00
[52] U.S. Cl. ............................... 367/173; 73/40.5 A; 73/622; 73/644; 24/20 TT; 24/68 D
[58] Field of Search ................ 181/140, 400; 340/8 S, 340/17 R; 73/40.5 A, 622, 644; 24/20 TT, 20 R, 68 D; 367/173

[56] References Cited

U.S. PATENT DOCUMENTS

| | | | |
|---|---|---|---|
| 2,908,161 | 10/1959 | Bincer | 73/622 |
| 3,883,841 | 5/1975 | Norel et al. | 367/25 |
| 4,021,773 | 10/1974 | Keenan | 340/8 S |

FOREIGN PATENT DOCUMENTS 1168349  10/1969  United Kingdom ................... 24/68 D

*Primary Examiner*—Howard A. Birmiel
*Attorney, Agent, or Firm*—Gerald J. Ferguson, Jr.; Joseph J. Baker

[57] ABSTRACT

Apparatus for fixing a sonic or ultrasonic transducer to a container. The transducer is arranged axially displaceable in the recess in a holder. A spring is mounted in the recess, which attempts to urge the transducer outwards. On both sides of the transducer, the holder is connected to a clamping strip for passing around the periphery of the container. At least one of the two connections between the holder and the clamping strip is formed by a clamping device for tightening the clamping strip. The clamping device includes a spring determining the clamping force of the clamping strip.

12 Claims, 4 Drawing Figures

FIXING OF SONIC TRANSDUCER TO A CONTAINER

The invention relates to an apparatus for fixing a sonic or ultrasonic transducer to a container.

Filling level limit switches are known in which a sonic or ultrasonic transducer is so fixed to the outside of the container wall at the filling level to be established that it transmits sonic or ultrasonic pulses through the container wall and can receive the echo pulses reflected from the opposite container wall. Since the propagation conditions for sonic and ultrasonic waves in air are very different from the propagation conditions in other media, especially liquids, the reception or absence of echo pulses can be used as a criterian therefor as to whether air or filling material is located between the transducer and the opposite container wall thus as to whether the filling level is exceeded or not yet reached and which is determined by the level at which the sonic or ultrasonic transducer is mounted on the container.

Fixing of the transducer to the outside of the container is of advantage because in many cases an aperture in the container wall is undesirable or even inadmissable. In order to guarantee perfect transmission of the sonic or ultrasonic waves between the transducer and the container wall care must indeed be taken that the active area of the transducer engages the container wall under a predetermined contact pressure wherein the said contact pressure remains constant even with changing operating conditions, especially with temperature variations. Fulfilling this requirement is made difficult by the fact that suitable mounting arrangements are not provided on most containers and in general cannot even be provided for in advance because the limit filling level to be ascertained can vary from case to case and is often only determined at the place of installation; it may even be assumed that the mounting position of the transducer on the same container must be removed after some time to suit different operating conditions. In all cases, it must be possible to remove the transducer for cleaning purposes and then to mount it once again at the same position whilst guaranteeing the correct contact pressure. Fixing apparatus must be so designed that such maintenance operations can be undertaken by the user of the equipment himself. Furthermore, with already installed containers, it is generally not possible to provide fixing arrangements on the container wall whereby a subsequent provision of sonic or ultrasonic limit switches is made more difficult.

An object of the invention is the provision of an apparatus with which a sonic or ultrasonic transducer can be fixed in any desired position whilst achieving the defined constant contact pressure on the outer surface of containers of desired form and size even with changing operating conditions without operations or variations having to be undertaken at the container itself.

This problem is solved in accordance with the invention in that the transducer is arrangement axially displaceable in the recess in a holder, that a spring is arranged in the recess which attempts to urge the transducer outwards, that, on both sides of the transducer, the holder is associated with a clamping strip to be applied around the periphery of the container, but at least one of the two connections between the holder and the clamping strip is formed by a clamping device for tightening the clamping strip and that the clamping device includes a spring determining the clamping force of the clamping strip.

With the apparatus according to the invention, a sonic or ultrasonic transducer can be mounted at any desired position on the outer wall of a container of any shape and size without the need to undertake operations or modifications to the container itself; the only provision in this connection is that the clamping strip can be applied around the container. In that way, it is possible for the mounting of the transducer at the installation location to fit the prevailing operating conditions and to be varied according to needs. Furthermore, even already installed containers can be subsequently provided with a sonic or ultrasonic limit switch. The spring acting on the transducer guarantees a uniform contact pressure of the transducer against the container and the spring determining the clamping force of the clamping strip compensates for variations in length which can occur especially due to different coefficient of heat expansion of the container and the clamping strip. The mounting is simple and can even be undertaken by persons without special skill; thereby, it is possible for the user of the equipment, for example, to vary the mounting position of the transducer according to needs.

Figure 2:
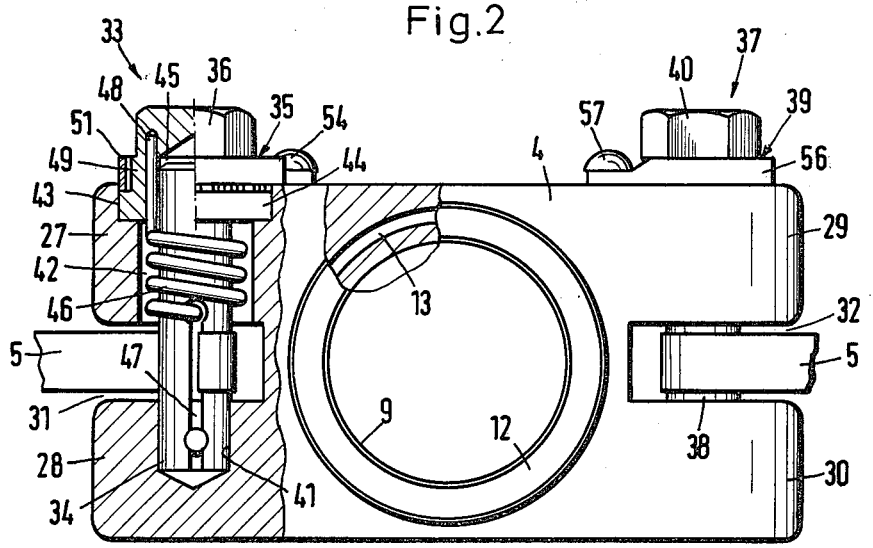
Figure 3:
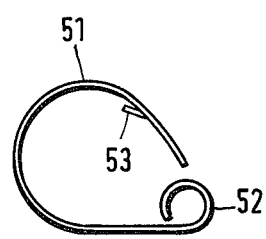
Figure 4:
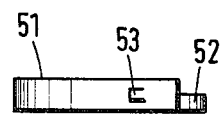

Further features and advantages of the invention will become apparent from the following description of embodiments with the aid of the drawing. In the drawings:

FIG. 1 is a sectional view of the holder with the sonic or ultrasonic transducer mounted therein, FIG. 2 is a part section view of the holder from the side remote from the container with the cover taken off and the transducer removed, FIG. 3 is a planned view of the leaf spring of the locking teeth and FIG. 4 is a side view of the leaf spring in FIG. 3.

A sonic or ultrasonic transducer 1 is illustrated in FIG. 1 the end surface 2 of which is designed for engagement with a container 3 illustrated schematically in FIG. 1. For fixing the transducer 1 to the container 3 a holder 4 is provided which can be fixed to the container by means of a clamping strip 5 arranged around the container and the transducer is thereby urged into engagement with the wall of the container.

The transducer 1 has a transducer head 6 of circular cross section to which the end surface 2 is applied, and a cylindrical section 7 of smaller diameter extending from the transducer head from which extends a cylindrical section 8 of still smaller diameter. The holder 4 has a cylindrical recess 9 for receiving the transducer and which extends throught the holder 4 and the cross section of which matches the cross section of the transducer head 6 so that the transducer head 6 can slide in the cylindrical recess 9. At the rear end remote from the container 3, the holder 4 carries a cover 10 provided with a bevelled edge 11 which engages the rear of the holder 4 through a cylindrical section 12. An annular groove 13 is formed in the cylindrical section 12 and the edge 11 is provided with three threaded openings 14 arranged at an angular distance of 120° from each other, only one of which is visible in FIG. 1. A threaded pin 15 with a conical point which engages in the annular groove 13, is screwed into each of the said threaded openings. The cover 10 has a central opening 16 through which the cylindrical section 8 of the transducer slidably passes. An O-ring 17 inserted in an annular groove in the central opening 16, serves for sealing the interior of the holder 4 against environmental influences, for example against splashing.

A helical compression spring 18, which surrounds the cylindrical section 7 of the transducer is arranged inside the recess 9 of the transducer and is supported on the one hand on the shoulder surface of the transducer head 6 and on the other hand on the inner surface of the cover 10 with the inter position of a packing ring 19. The compression spring 18 attempts to urge the transducer 1 into the recess 9 towards the container 3. This displacement is limited by a split ring 20 which is inserted in an annular groove on the portion of the cylindrical section 8 lying outside the cover 10. The dimensions of the holder are so selected with respect to the dimensions of the transducer that when the holder 4 is not fixed to the container 3, the end surface 2 of the transducer 1 in its most forward limit position which is determined by the abutment of the split ring 20 against the cover 10, projects to some extent beyond the end surface 21 of the holder facing the container.

A recess 22 with straight side walls which is wider than the sylindrical recess 9, is cut into the front end of the holder 4 facing the container 3 and over its entire height, so that a free intermediate space exists on both sides of the transducer head. A ring 23 of elastic material, for example silicone rubber, is so arranged in the recess 22 that it surrounds the transducer head 6 with a slight clearance. The ring 23, which, for example, is about 15 mm high and about 3 mm thick, is inserted in an annular groove 24 at the base of the recess 22 and its height is so calculated that in its undeformed condition, which is illustrated in FIG. 1, projects beyond the end surface 21 of the holder 4 by approximately the same amount as the end surface 2 of the transducer 1. The two straight side edges of the recess 22 are inclined by a chamfer 25.

The electrical connecting cable 26 for the transducer 1 is led outwards through the end of the cylindrical section 8 of the transducer 1 projecting rearwardly from the cover 10. On the holder 4, at each side of the cylindrical recess 9, there are formed two laterally extending bearing attachments 27, 28 or 29, 30 between which there exists an intermediate space 31 or 32. A clamping device 33, which has a winding mandrel 34 to which one end of the clamping strip 5 is anchored in the intermediate space 31, is mounted in the bearing extensions 27, 28. By means of a rotary part 35 which has a hexagonal head 36 for receiving a spanner, the winding mandrel 34 can be rotated so that the clamping strip 5 is wound thereon. In the same manner, a clamping device 37 is mounted in the bearing extensions 29 and 30 and which has a winding mandrel 38 and a rotary part 39 with an hexagonal head 40 whereby the other end of the clamping strip 5 is anchored to the section of the winding mandrel 38 freely lying in the intermediate space 32.

The two clamping devices 33 and 37 are made exactly the same; thus, only the construction of the clamping device 33 will be described in detail in the following.

A bearing bore 41 which matches the diameter of the winding mandrel 34, is arranged in the lower bearing extension 28; the lower end of the winding mandrel 34 is rotatably mounted in the bearing bore 41. On the other hand, a bore 42 the diameter of which is considerably greater than the diameter of the winding mandrel 34, is formed in the upper bearing extension 27. A stepped windening 43 in which is rotatably mounted a cylindrical section 44 on the lower end of the rotary part 35, is formed at the upper end of the bore 42. A downwardly open recess 45 the diameter of which fits the diameter of the winding mandrel 34 and in which the upper end of the winding mandrel 34 is rotatably mounted, is formed in the rotary part 35. Thus, the rotary part 35 is rotatably mounted in the stepped widening 43 relatively to the holder 4 and the winding mandrel 34 is rotatably mounted in the bearing bore 41 and is rotatably mounted in the recess 45 not only with respect to the holder 4 but also relatively to the rotary part 35.

Within the bore 42, the winding mandrel 34 is surrounded by an helical spring 46 which is connected at one end for rotation with the winding mandrel 34 and is connected at the other end for rotation with the rotary part 35. The lower end of the helical spring 46 is bent diametrally and sits in a diametral slot 47 which is cut in substantially over half its height away from the lower end of the winding mandrel 34. The upper end 48 of the helical spring 46 is bent parallel to the axis and is accomodated in a correspondingly shaped recess in the rotary part 35. This construction permits an easy mounting: the helical spring 46 is pushed over the winding mandrel 34 from the lower end so that its diametrally bent lower end slides upwards into the slot 47; after the winding mandrel 34 has been inserted in the bores 41 and 42, the rotary part 35 can be so pushed over the upper end of the winding mandrel 34 and be inserted in the widening 43 that the axially bent end 48 of the helical spring 46 enters into the corresponding recess in the rotary part 35.

As is to be understood, the helical spring 46 forms a torque transmitting coupling element between the rotary part 35 and the winding mandrel 34.

In addition, the diametral slot 47 serves for anchoring the clamping strips the end of which bent at right angles is hooked into the slot 47.

The intermediate section 49 of the rotary part 35 lying between cylindrical section 44 and the hexagonal head 36, is formed on the outside with a ring of locking teeth 50 extending around the periphery (FIG. 1). These locking teeth are surrounded over more than half the periphery by a leaf spring 51 which is illustrated more specifically in FIGS. 3 and 4 in top and side views respectively. One end of the leaf spring, which is reduced width, is bent into a round eye 52. At the other end section, a tongue 53 is separated therefrom by a U shaped insition which is bent inwards away from the surface of the leaf spring. The eye 52 is anchored to the holder 4 by means of a notched pin 54. The tongue 53 cooperates with the locking teeth 50 so that the thus formed pawl and ratchet permits a rotation of the rotary part 35 in the clockwise sense (in FIG. 1), but prevents a rotation in the opposite sense. Upon rotation in the clockwise sense, the pawl 53 can slide over the teeth of the locking teeth 50 as a result of elasticity of the leaf spring 51 whereas upon a rotation in the opposite sense, it latches in the locking teeth.

The clamping device 37 is provided with a pawl and ratchet of the same type which consists of locking teeth 55 formed on the rotary part 39 and a leaf spring 56 cooperating therewith. The leaf spring 56 is exactly the same as the leaf spring 55 illustrated in FIGS. 3 and 4 and is anchored to the holder 4 by means of a notched pin 57.

For mounting the transducer 1 in the desired position on a container 3, the holder 4, in which the transducer is mounted in the manner illustrated in FIG. 1, is applied at the desired location to the outside of the container and the clamping strip 5 is passed around the container and is suspended at both ends in the winding mandrels 34 and 38. By rotating the rotary parts 35 and 39 with the aid of a spanner engaging the hexagonal heads 36, 40, a clamping strip 5 is wound onto the winding mandrels from both ends. Then, only the active end surface 2 of the transducer 1 and the end surface of the elastic ring 23 engage the outer surface of the container 3 (FIG. 1). When the area of the container facing the transducer is flat the contact is over an area; however, in most cases the outer surfaces of the container is curved so that the contact takes place only along a surface line of the container. The active end area 2 of the transducer is covered with a 1 to 2 mm thick layer of a sealing compound which is smeared with a silicone grease before the transducer is mounted. By this means, the transmission of the sonic or ultrasonic waves from the transducer 1 to the container wall and vice versa and is promoted.

When the clamping strip 5 is stretched around the container 3 and the rotation of the rotary parts 35 and 39 is continued, the clamping strip 5 tightens the whole of 4 against the container against the force of the helical compression spring 18 which is supported by the container 3 through the transducer head 6. Thus, the transducer 1 is forced inwards into the recess 9 with compression of the helical compression spring 18 and the elastic ring 23 is increasingly deformed until it finally engages the wall of the container 3 over its entire periphery. The clamping strip 5 is tightened still further until finally the holder 4 engages the outer surface of the container 3. And indeed, in the case of a flat outer surface, by means of its end surface 21 or, in the case of a curved outer surface, along the chamfer 25 at the side edges of the recess 22. In this position, the contact pressure at which the end surface 2 of the transducer 1 is urged against the outer surface of the container 3 is determined by the degree of compression of the helical compression spring 18 then reached which is positively defined by the geometrical dimensions of the various parts. The elastic ring 23 is compressed in such a manner that it tightly engages the wall of the container 3 around the transducer head 6 even when the wall is curved. In that manner, especially the contact point between the active end surface 2 of the transducer and the container wall as well as the sealing compound and layer of silicone grease applied to the active end surface, is protected against environmental influences such as splashing or the like as well as even against mechanical damage.

On further rotation of the rotary parts 35 and 39 by means of a spanner, the clamping strip 5 cannot be wound any further onto the winding mandrel 34 and 38; instead, the springs 46 transmitting the torque are then tensioned. This is continued until a pre-tensioning is imparted to the springs 46 which is sufficient to take up all possibly occuring variations in length which can be produced in particular by different coefficience of heat expansion of the clamping strip 5 and the container 3 with variations in temperature.

Latching of the pawl 53 on the leaf spring 51 or 56 in the locking teeth 50 or 55 prevents a back rotation of the spring 46 of each clamping device.

The active end surface 2 of the transducer is urged against the container wall 3 by a contact pressure acurately defined by the degree of compression of the helical compression spring 18 and always remaining the same. Even when the holder 4 together with transducer 1 is removed from the container 3 and is then mounted in the same position or at another new position, the same contact pressure is reproduced with good accuracy.

The tensile force produced in the clamping strip 5 is transmitted to the holder 4 through the winding mandrel 34, 38 and the rotary parts 35, 39. The helical springs 46 mounted on the two winding mandrels 34, 38 are under a spring tension which corresponds to the torque exerted on the winding mandrels by the said tensile stress. Thus, the tensile stress produced is maintained substantially constant even when different variations in length occur as a result of the different coefficience of heat expansion of the clamping strip and the clamping wall. Each of the two helical springs 46 can compensate for a variation in the length of about 10 mm. Thus, there is a guarantee that the holder 4 and with it the transducer 1 is always rigidly held against the container wall with a uniformed tensile force even with different heat expansions.

The cover 10 can be removed from the holder 4 by loosening the three threaded pins 15. It is thereby possible to remove the transducer 1 from the holder 4 without the latter being removed from the container 3 and without having to loosen the clamping strip 5. If the same or another transducer 1 is then inserted once again in the cylindrical recess 9 in the holder 4 and the cover 10 is fixed, the same constant contact pressure for the transducer 1 is again guaranteed by the compression of the helical compression spring 18.

The clamping strip 5 can also be released from the container 3 in a simple manner by counter rotating the hexagonal heads 36, 40; for this purpose, the leaf spring 31 or 56 is urged outwardly to some extent by means of a screw driver so that the pawl mounted thereon releases the locking teeth 50 or 55. Then, the entire holder 4 can be removed from the container or be displaced into another position.

Practical tests have shown that the constant contact pressure of the transducer can also be maintained when the holder 4 is subjected to a lateral load (perpendicular to the plane of the drawing in FIG. 1). Such loads can occur, in particular with embodiments in which, instead of the connecting gable 26, a housing accommodating the electronic equipment is mounted directly on the holder 4.

What we claim is:

1. A device for fixing a sonic or ultrasonic transducer to a container, comprising a holder adapted to be applied to the outside of the container and having an internal recess which is open towards the container and in which said transducer is arranged axially displaceable, a first spring mounted in said recess so as to urge said transducer outward towards the container, and a clamping strip extending around the periphery of said container and connected to said holder by connecting members at both sides of said transducer for clamping the holder to the container and for maintaining the transducer in contact with the container, at least one of said connecting members including a tensioning device for tightening said clamping strip, said tensioning device including a second spring for determining the clamping force of said clamping strip without affecting the contact pressure of the transducer with respect to the container.

2. A device according to claim 1 in which said tensioning device has a winding mandrel which is rotatably mounted in bearing extensions laterally projecting from the holder and in which the end of the clamping strip is anchored, a rotary member being mounted on the bearing extension coaxial to the winding mandrel and connected to the winding mandrel by said second spring which is a torque transmitting spring.

3. A device according to claim 2 in which said second spring is a helical spring which surrounds a section of the winding mandrel and which is anchored to the winding mandrel by a diametrially bent end and is anchored to the rotary member at the other end.

4. A device according to claim 2 in which said rotary member has an axial recess in which one end of said winding mandrel is rotatably mounted.

5. A device according to claim 2 in which a pawl and ratchet permitting rotation in only one sense is arranged between the rotary member and the holder.

6. A device according to claim 5 in which the pawl and ratchet is formed by locking teeth applied coaxially to said rotary member and by a leaf spring surrounding the locking teeth over more than 180° of their periphery, the leaf spring carrying a pawl and being anchored at one end to the holder.

7. A device according to claim 6 in which said pawl is formed by an inwardly bent section of the leaf spring partially separated by an incision.

8. A device according to claim 2 in which said connecting members each include said tensioning device mounted in the bearing extension on each side of the holder.

9. A device according to claim 1 in which the recess in the holder accommodating the transducer is formed by an opening passing completely through the holder the cross section of which opening matches the largest cross section of the transducer, the end remote from the container being closed by a cover releasably fixed to the holder, and in which said first spring is a helical compression spring which inside the recess surrounds a cylindrical section of the transducer having a reduced diameter and bears against said cover.

10. A device according to claims 1 or 9 in which a ring of elastic material surrounding the transducer projects from the end surface of the holder facing the container.

11. A device according to claim 10 in which said ring cnsists of silicone rubber.

12. A device according to claim 10 in which said ring is arranged in an annular enlarged portion of the recess surrounding the transducer.

* * * * *